(12) United States Patent
Magalhaes et al.

(10) Patent No.: US 10,617,914 B1
(45) Date of Patent: Apr. 14, 2020

(54) TRAINING AID

(71) Applicants: Gabriel Magalhaes, Palmetto Bay, FL (US); Filipe Magalhaes, Palmetto Bay, FL (US)

(72) Inventors: Gabriel Magalhaes, Palmetto Bay, FL (US); Filipe Magalhaes, Palmetto Bay, FL (US)

( * ) Notice: Subject to any disclaimer, the term of this patent is extended or adjusted under 35 U.S.C. 154(b) by 0 days.

(21) Appl. No.: 16/140,656

(22) Filed: Sep. 25, 2018

(51) Int. Cl.
*A63B 33/00* (2006.01)
*A61F 9/02* (2006.01)
*A63B 71/06* (2006.01)

(52) U.S. Cl.
CPC ............ *A63B 33/002* (2013.01); *A61F 9/029* (2013.01); *A63B 71/0686* (2013.01); *A63B 2033/004* (2013.01); *A63B 2071/0666* (2013.01)

(58) Field of Classification Search
CPC .............. A63B 33/002; A63B 71/0686; A63B 2033/004; A63B 2071/0666; A61F 9/029
See application file for complete search history.

(56) References Cited

U.S. PATENT DOCUMENTS

| | | | |
|---|---|---|---|
| 4,753,514 A * | 6/1988 | Kubik | G02C 9/04 351/158 |
| 4,796,987 A | 1/1989 | Linden | |
| 5,402,188 A * | 3/1995 | Wayne | A63B 33/002 351/43 |
| 5,446,506 A | 8/1995 | Dawklins | |
| 5,585,871 A | 12/1996 | Linden | |
| 5,685,722 A | 11/1997 | Taba | |
| 5,697,792 A | 12/1997 | Ladin | |
| 6,431,705 B1 * | 8/2002 | Linden | G02C 11/00 351/158 |
| D470,880 S | 2/2003 | Sakai | |
| 7,081,809 B1 * | 7/2006 | Mix | A63B 71/0686 2/426 |
| 7,185,983 B2 | 3/2007 | Nelson | |
| 7,192,137 B2 * | 3/2007 | Ishibashi | A61F 9/02 351/158 |
| 9,001,005 B2 * | 4/2015 | Abdollahi | G02B 27/0176 345/7 |
| 9,069,166 B2 * | 6/2015 | Abdollahi | G02B 27/0172 |
| 10,012,506 B1 * | 7/2018 | Monahan | G02C 11/10 |
| 2014/0213917 A1 * | 7/2014 | Hobeika | A61B 5/02416 600/500 |
| 2017/0046979 A1 * | 2/2017 | Lehary | H04B 1/3888 |
| 2017/0333752 A1 * | 11/2017 | Korkala | A63B 71/0686 |
| 2018/0001182 A1 * | 1/2018 | Szanto | A63B 71/0686 |

\* cited by examiner

*Primary Examiner* — Quan-Zhen Wang
*Assistant Examiner* — Rajsheed O Black-Childress

(57) ABSTRACT

A training aid for a swimmer includes a housing. The housing is sealed so that the housing is water tight. A coupler is coupled to the housing and is configured to couple to a swimmer's goggles to couple the housing to the goggles. A power module, a microprocessor, and a sensor are coupled to and positioned in the housing. An indicator is coupled to the housing. The microprocessor is operationally coupled to the power module. The sensor and the indicator are operationally coupled to the microprocessor. The sensor is configured to detect motion of the housing so that the microprocessor is positioned to determine a speed of the swimmer and to compare performance values of the swimmer relative to target values. The microprocessor is positioned to selectively signal the indicator to notify the swimmer of a difference between the performance values and the target values.

16 Claims, 5 Drawing Sheets

TRAINING AID

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

(2) Description of Related Art Including Information Disclosed Under 37 CFR 1.97 and 1.98

The disclosure and prior art relates to training aids and more particularly pertains to a new training aid for a swimmer.

BRIEF SUMMARY OF THE INVENTION

An embodiment of the disclosure meets the needs presented above by generally comprising a housing. The housing is sealed so that the housing is water tight. A coupler is coupled to the housing and is configured to couple to a swimmer's goggles to couple the housing to the goggles. A power module, a microprocessor, and a sensor are coupled to and positioned in the housing. An indicator is coupled to the housing. The microprocessor is operationally coupled to the power module. The sensor and the indicator are operationally coupled to the microprocessor. The sensor is configured to detect motion of the housing so that the microprocessor is positioned to determine a speed of the swimmer and to compare performance values of the swimmer relative to target values. The microprocessor is positioned to selectively signal the indicator to notify the swimmer of a difference between the performance values and the target values.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
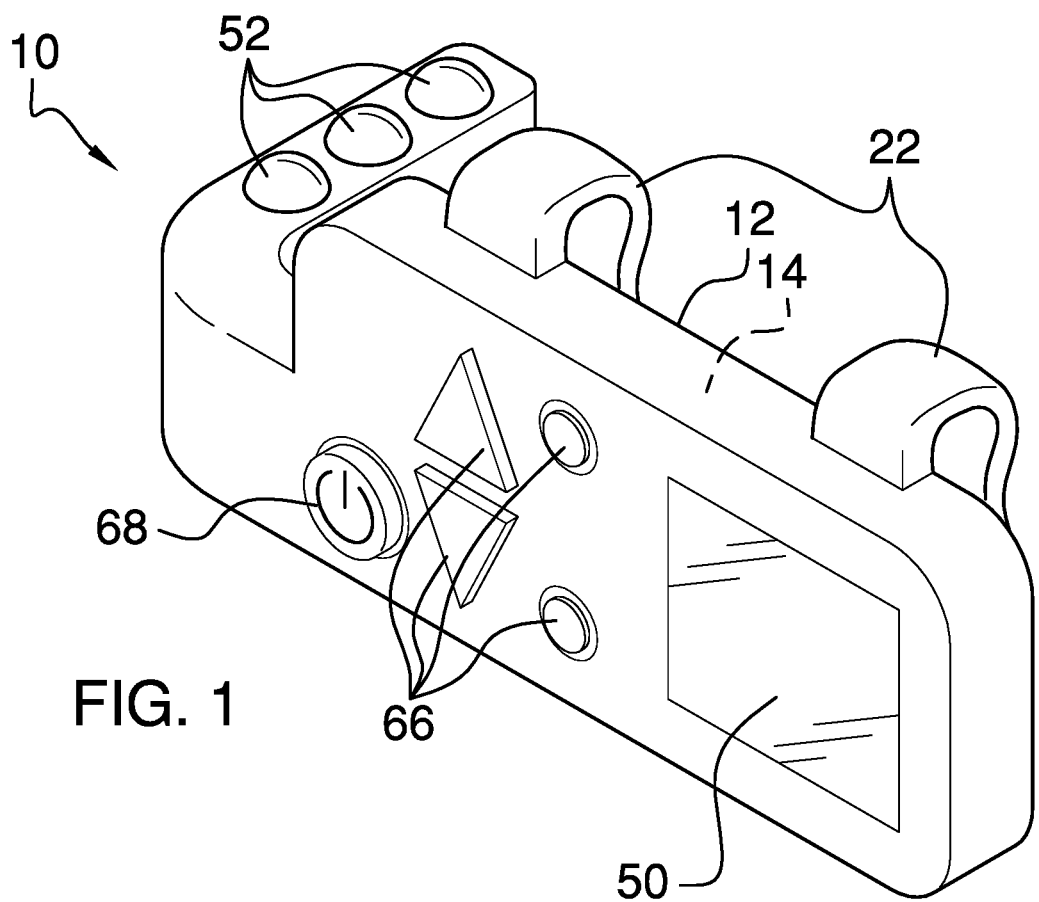
FIG. 1 is an isometric perspective view of a training aid according to an embodiment of the disclosure.

With reference now to the drawings, and in particular to FIGS. 1 through 7 thereof, a new training aid embodying the principles and concepts of an embodiment of the disclosure and generally designated by the reference numeral 10 will be described.

Figure 2:
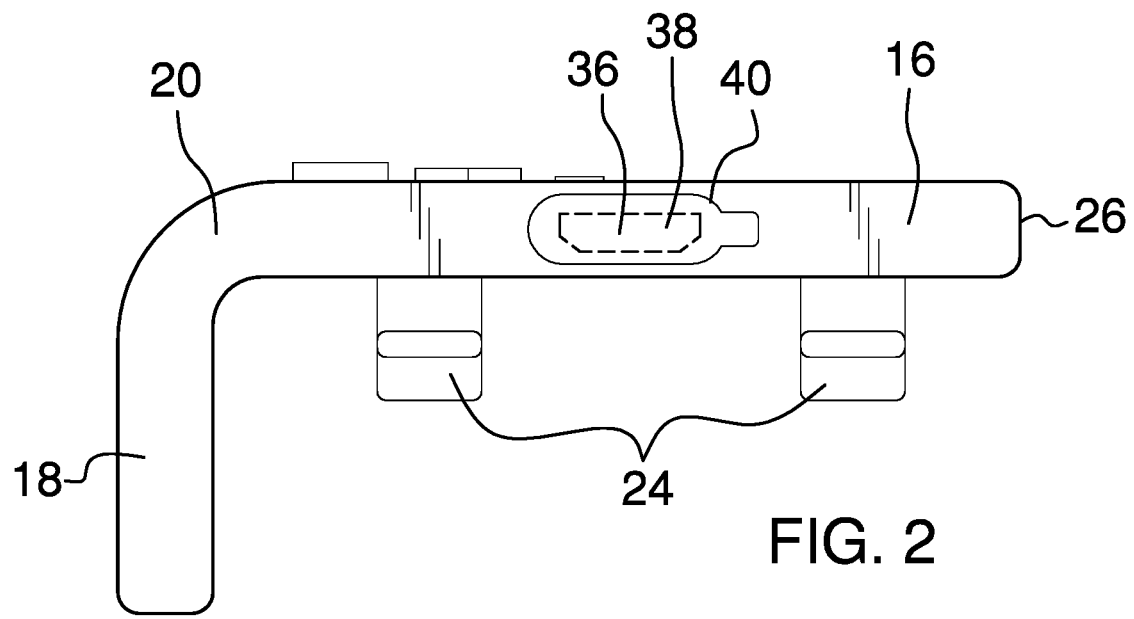
FIG. 2 is a bottom view of an embodiment of the disclosure.

As best illustrated in FIGS. 1 through 7, the training aid 10 generally comprises a housing 12 that defines an interior space 14. The housing 12 is sealed so that the housing 12 is water tight. The housing 12 comprises plastic. The housing 12 comprises a first section 16 and a second section 18. The second section 18 is coupled to and extends perpendicularly from a first end 20 of the first section 16, as shown in FIG. 2. The first section 16 and the second section 18 are substantially rectangularly box shaped.

A coupler 22 is coupled to the housing 12. The coupler 22 is configured to couple to a swimmer's goggles so that the coupler 22 is configured to couple the housing 12 to the goggles. The coupler 22 comprises a plurality of clips 24. The clips 24 are resilient so that the clips 24 are configured to insert a band of the goggles to couple the housing 12 to the band. The plurality of clips 24 comprises two clips 24. The clips 24 are positioned singly proximate to the first end 20 and a second end 26 of the first section 16. The clips 24 are positioned on a first face 28 of the first section 16 of the housing 12. It also is anticipated that the housing 12 is integral to a pair of swimming goggles 30.

A power module 32 is coupled to the housing 12 and is positioned in the interior space 14. The power module 32 comprises a battery 34. The battery 34 is rechargeable. A port 36 is positioned in the housing 12. The port 36 is operationally coupled to the battery 34 so that the port 36 is configured to couple the battery 34 to a source of direct current to recharge the battery 34. The port 36 comprises a universal serial bus port 38, as shown in FIG. 2. A panel 40 is coupled to the housing 12 proximate to the port 36. The panel 40 is configured to couple to the housing 12 so that the panel 40 is positioned to sealably close the port 36 as shown in FIG. 2.

A microprocessor 42, a timer 44, a sensor 46, and a vibrator 48 are coupled to the housing 12 and are positioned in the interior space 14. The microprocessor 42 is operationally coupled to the power module 32. The timer 44, the sensor 46, and the vibrator 48 are operationally coupled to the microprocessor 42. The timer 44 is configured to communicate an elapsed time to the microprocessor 42 to provide stopwatch functionality.

Figure 3:
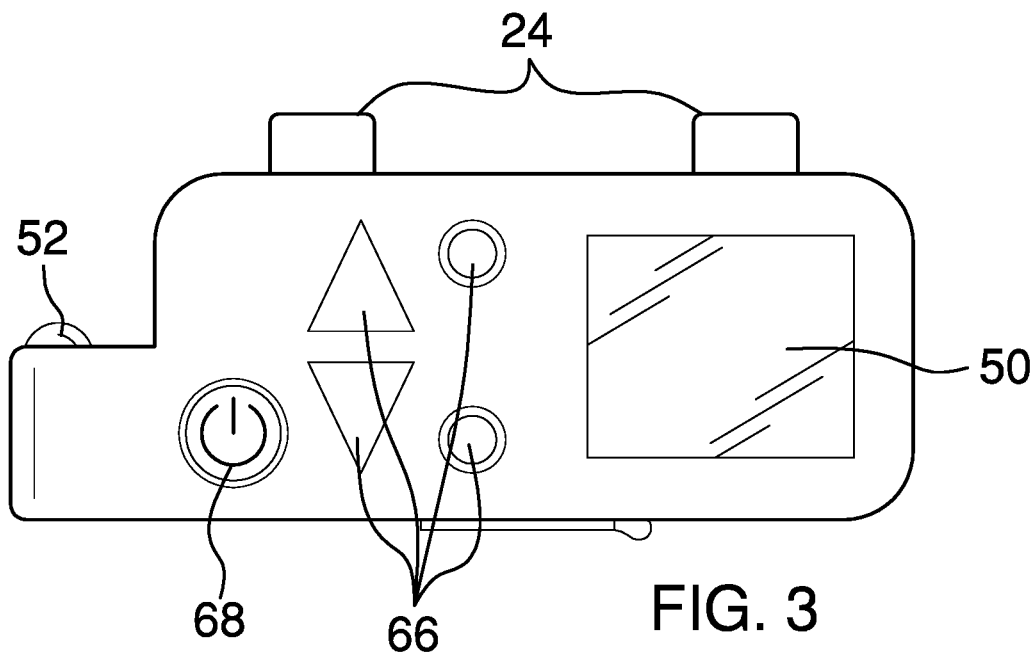
FIG. 3 is a front view of an embodiment of the disclosure.
Figure 4:
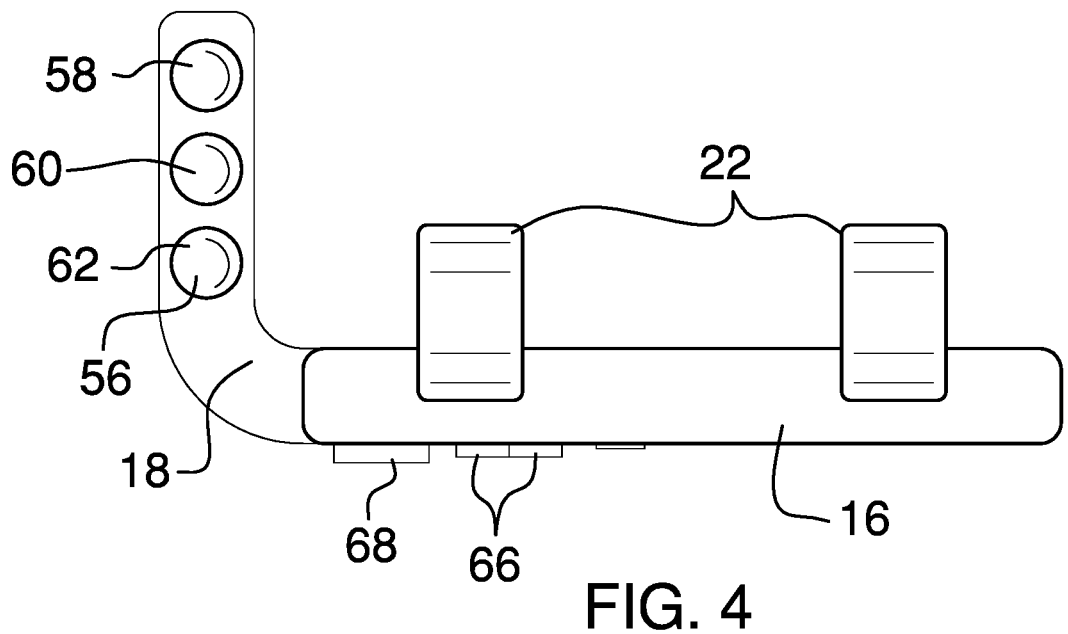
FIG. 4 is a top view of an embodiment of the disclosure.
Figure 5:
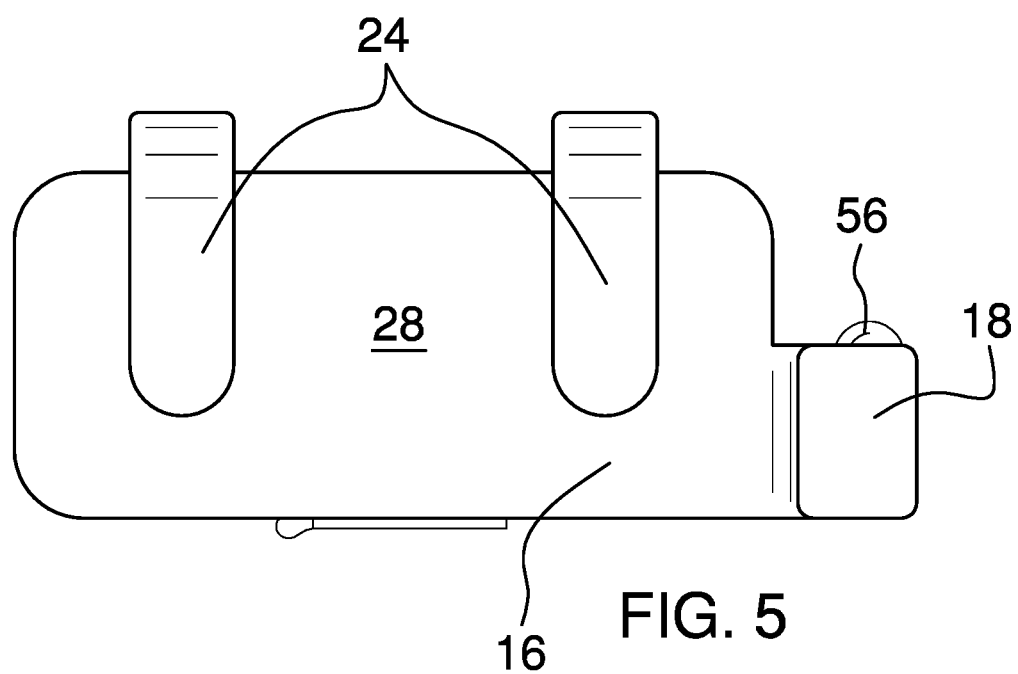
FIG. 5 is a back view of an embodiment of the disclosure.
Figure 6:
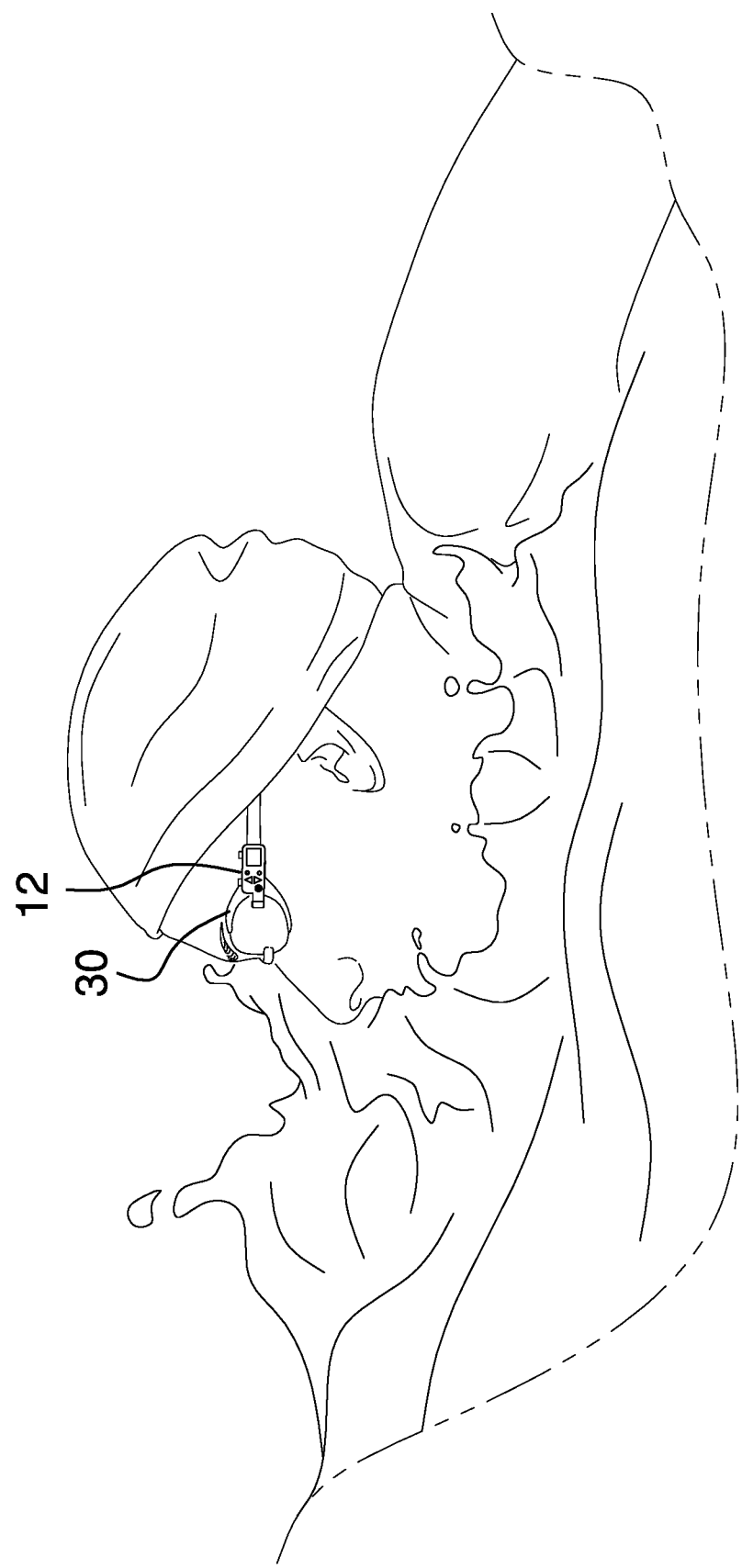
FIG. 6 is an in-use view of an embodiment of the disclosure.
Figure 7:
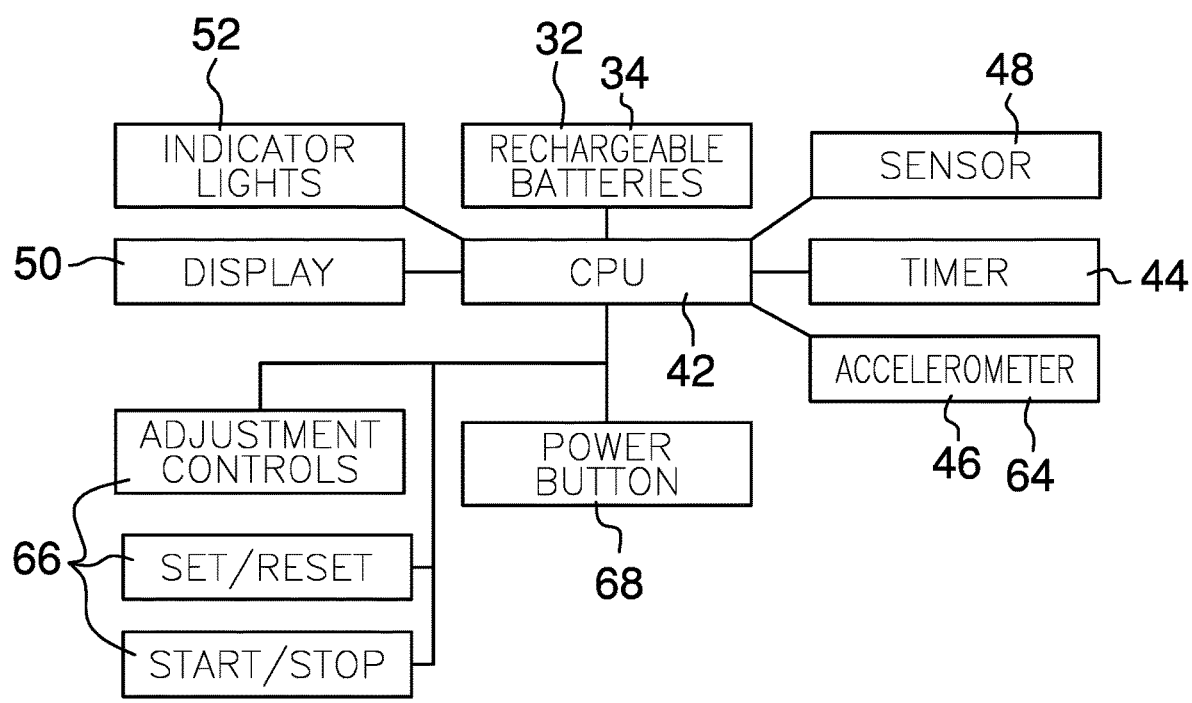
FIG. 7 is a block diagram of an embodiment of the disclosure.

A display 50 and an indicator 52 are coupled to the housing 12, as shown in FIGS. 3 and 4, respectively. The indicator 52 and the display 50 are operationally coupled to the microprocessor 42. The indicator 52 comprises a plurality of bulbs 54 that is coupled to the second section 18 of the housing 12 so that the bulbs 54 are visible to the swimmer. Each bulb 54 emits a respective color so that the plurality of bulbs 54 is configured to emit a variety of colors. Each of the plurality of bulbs 54 comprises a light emitting diode 56. The plurality of bulbs 54 comprises a first light 58 that is green, a second light 60 that is yellow, and a third light 62 that is red.

The sensor 46 is configured to detect motion of the housing 12 so that the microprocessor 42 is positioned to determine a speed of the swimmer and to compare performance values of the swimmer relative to target values. The microprocessor 42 is positioned to selectively signal the indicator 52 to notify the swimmer of a difference between the performance values and the target values. The microprocessor 42 also is positioned to signal the vibrator 48 to selectively vibrate to notify the swimmer of a difference between the performance values and the target values. The sensor 46 comprises an accelerometer 64 that communicates acceleration data for the housing 12, and thus the swimmer, to the microprocessor 42. The microprocessor 42 processes the acceleration data to determine the speed of the swimmer.

A controller 66 is coupled to the housing 12 as shown in FIG. 3. The controller 66 is operationally coupled to the microprocessor 42. The controller 66 is positioned to enter the target values for the performance of the swimmer and to select output variables to present on the display 50. For example, the swimmer uses the controller 66 to program the microprocessor 42 to illuminate the third light 62 when the performance values are ten percent or more below the target values, the second light 60 when the performance values are within a range of five to ten percent below the target values, and the first light 58 when the performance values within a range of zero to five percent below the target values. In this example, the none of the plurality of bulbs 54 would be illuminated if the swimmer was swimming fast enough to meet or exceed the target values. The controller 66 also is positioned to select between use of the plurality of bulbs 54 and the vibrator 48 for notifying the swimmer of the difference between the performance values and the target values.

When the swimmer has completed the training exercise, the swimmer is positioned to utilize the controller 66 to command the microprocessor 42 to signal the display 50 to present the difference between the performance values and the target values, along with the time elapsed, lap count, and other performance parameters.

A power button 68 is coupled to the housing 12. The power button 68 is operationally coupled to the microprocessor 42 and the power module 32. The power button 68 is depressible. The power button 68 is configured to be depressed a first time to operationally couple the microprocessor 42 to the power module 32. The power button 68 is configured to be depressed a second time to decouple the microprocessor 42 from the power module 32.

In use, the clips 24 are configured to insert the band of the goggles to couple the housing 12 to the band. The controller 66 is positioned to enter the target values for the performance of the swimmer and to select the output variables to present on the display 50. The microprocessor 42 is positioned to determine the speed of the swimmer and to compare the performance values of the swimmer relative to the target values. The microprocessor 42 is positioned to selectively signal the indicator 52 to notify the swimmer of the difference between the performance values and the target values.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

We claim:

1. A training aid comprising:
a housing defining an interior space, said housing being sealed such that said housing is water tight, said housing comprising a first section and a second section, said second section being coupled to and extending perpendicularly from a first end of said first section;
a coupler coupled to said housing, said coupler being configured for coupling to a swimmer's goggles wherein said coupler is configured for coupling said housing to the goggles;
a power module coupled to said housing and positioned in said interior space;
a microprocessor coupled to said housing and positioned in said interior space, said microprocessor being operationally coupled to said power module;
an indicator coupled to said housing, said indicator being operationally coupled to said microprocessor, said indicator comprising a plurality of bulbs coupled to said second section of said housing, said plurality of bulbs being spaced along a top surface of said second section and aligned parallel to a central longitudinal axis of said second section such that said bulbs are visible to the swimmer, each said bulb emitting a respective color such that said plurality of bulbs is configured for emitting a variety of colors;
a sensor coupled to said housing and positioned in said interior space, said sensor being operationally coupled to said microprocessor, said sensor being configured for detecting motion of said housing; and wherein said microprocessor is positioned for determining a speed of the swimmer and for comparing performance values of the swimmer relative to target values such that said microprocessor is positioned for selectively signaling said indicator for notifying the swimmer of a difference between the performance values and the target values.

2. The aid of claim 1, further including said housing comprising plastic.

3. The aid of claim 1, further including said first section and said second section being substantially rectangularly box shaped.

4. The aid of claim 1, further including said housing being integral to a pair of swimming goggles.

5. The aid of claim 1, further including said coupler comprising a plurality of clips, said clips being resilient such that said clips are configured for inserting a band of the goggles for coupling said housing to the band.

6. The aid of claim 5, further including said plurality of clips comprising two said clips, said clips being positioned singly proximate to said first end and a second end of said first section, said clips being positioned on a first face of said first section of said housing.

7. The aid of claim 1, further comprising:
said power module comprising a battery, said battery being rechargeable;
a port positioned in said housing, said port being operationally coupled to said battery wherein said port is configured for coupling said battery to a source of direct current for recharging said battery; and
a panel coupled to said housing proximate to said port, said panel being configured for coupling to said housing such that said panel is positioned for sealably closing said port.

8. The aid of claim 7, further including said port comprising a universal serial bus port.

9. The aid of claim 1, further including a timer coupled to said housing and positioned in said interior space, said timer being operationally coupled to said microprocessor wherein said timer is configured for communicating an elapsed time to said microprocessor.

10. The aid of claim 1, further including each of said plurality of bulbs comprising a light emitting diode.

11. The aid of claim 10, further including said plurality of bulbs comprising a first light, a second light, and a third light, said first light being green, said second light being yellow, said third light being red.

12. The aid of claim 1, further including a display coupled to said housing, said display being operationally coupled to said microprocessor such that said microprocessor is positioned for signaling said display for presenting the difference between the performance values and the target values, said sensor comprising an accelerometer.

13. The aid of claim 1, further comprising:
a controller coupled to said housing, said controller being operationally coupled to said microprocessor wherein said controller is positioned for entering the target values for performance of the swimmer and for selecting output variables for presenting on said display; and
a power button coupled to said housing, said power button being operationally coupled to said microprocessor and said power module, said power button being depressible wherein said power button is configured for depressing a first time for operationally coupling said microprocessor to said power module and for depressing a second time for decoupling said microprocessor from said power module.

14. The aid of claim 1, further including a vibrator coupled to said housing and positioned in said interior space, said vibrator being operationally coupled to said microprocessor, wherein said vibrator is positioned in said housing such that said microprocessor is positioned for signaling said vibrator for selectively vibrating for notifying the swimmer of the difference between the difference between the performance values and the target values.

15. A training aid comprising:
a housing defining an interior space, said housing being sealed such that said housing is water tight, said housing comprising plastic, said housing comprising a first section and a second section, said second section being coupled to and extending perpendicularly from a first end of said first section, said first section and said second section being substantially rectangularly box shaped;
a coupler coupled to said housing, said coupler being configured for coupling to a swimmer's goggles wherein said coupler is configured for coupling said housing to the goggles, said coupler comprising a plurality of clips, said clips being resilient such that said clips are configured for inserting a band of the goggles for coupling said housing to the band, said plurality of clips comprising two said clips, said clips being positioned singly proximate to said first end and a second end of said first section, said clips being positioned on a first face of said first section of said housing;
a power module coupled to said housing and positioned in said interior space, said power module comprising a battery, said battery being rechargeable;
a port positioned in said housing, said port being operationally coupled to said battery wherein said port is configured for coupling said battery to a source of direct current for recharging said battery, said port comprising a universal serial bus port;
a panel coupled to said housing proximate to said port, said panel being configured for coupling to said housing such that said panel is positioned for sealably closing said port;
a microprocessor coupled to said housing and positioned in said interior space, said microprocessor being operationally coupled to said power module;
a timer coupled to said housing and positioned in said interior space, said timer being operationally coupled to said microprocessor wherein said timer is configured for communicating an elapsed time to said microprocessor;
an indicator coupled to said housing, said indicator being operationally coupled to said microprocessor, said indicator comprising a plurality of bulbs coupled to said second section of said housing, said plurality of bulbs being spaced along a top surface of said second section and aligned parallel to a central longitudinal axis of said second section such that said bulbs are visible to the swimmer, each said bulb emitting a respective color such that said plurality of bulbs is configured for emitting a variety of colors, each of said plurality of bulbs comprising a light emitting diode, said plurality of bulbs comprising a first light, a second light, and a third light, said first light being green, said second light being yellow, said third light being red,
a display coupled to said housing, said display being operationally coupled to said microprocessor;
a sensor coupled to said housing and positioned in said interior space, said sensor being operationally coupled to said microprocessor, said sensor being configured for detecting motion of said housing such that said microprocessor is positioned for determining a speed of the swimmer and for comparing performance values of the swimmer relative to target values such that said microprocessor is positioned for selectively signaling said indicator for notifying the swimmer of a difference between the performance values and the target values, such that said microprocessor is positioned for signaling said display for presenting the difference between the performance values and the target values, said sensor comprising an accelerometer;

a vibrator coupled to said housing and positioned in said interior space, said vibrator being operationally coupled to said microprocessor, wherein said vibrator is positioned in said housing such that said microprocessor is positioned for signaling said vibrator for selectively vibrating for notifying the swimmer of the difference between the difference between the performance values and the target values;

a controller coupled to said housing, said controller being operationally coupled to said microprocessor wherein said controller is positioned for entering the target values for performance of the swimmer and for selecting output variables for presenting on said display; and a power button coupled to said housing, said power button being operationally coupled to said microprocessor and said power module, said power button being depressible wherein said power button is configured for depressing a first time for operationally coupling said microprocessor to said power module and for depressing a second time for decoupling said microprocessor from said power module.

16. The aid of claim 15, further including said housing being integral to a pair of swimming goggles.

* * * * *